US010858353B2

(12) United States Patent
Oh et al.

(10) Patent No.: US 10,858,353 B2
(45) Date of Patent: Dec. 8, 2020

(54) INTERMEDIATES USEFUL FOR THE SYNTHESIS OF AMINOPYRIMIDINE DERIVATIVES, PROCESS FOR PREPARING THE SAME, AND PROCESS FOR PREPARING AMINOPYRIMIDINE DERIVATIVES USING THE SAME

(71) Applicant: Yuhan Corporation, Seoul (KR)

(72) Inventors: Sang-Ho Oh, Gyeonggi-do (KR); Ja-Heouk Khoo, Gyeonggi-do (KR); Jong-Chul Lim, Gyeonggi-do (KR); Doo-Byung Lee, Gyeonggi-do (KR); Jung-Ae Lee, Seoul (KR); Jun-Sup Lee, Gyeonggi-do (KR); Hyun Ju, Gyeonggi-do (KR); Woo-Seob Shin, Gyeonggi-do (KR); Sang-Seol Jeon, Gyeonggi-do (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 16/633,695

(22) PCT Filed: Jul. 25, 2018

(86) PCT No.: PCT/KR2018/008381
§ 371 (c)(1),
(2) Date: Jan. 24, 2020

(87) PCT Pub. No.: WO2019/022486
PCT Pub. Date: Jan. 31, 2019

(65) Prior Publication Data
US 2020/0207750 A1     Jul. 2, 2020

(30) Foreign Application Priority Data

Jul. 28, 2017    (KR) ..................... 10-2017-0096220

(51) Int. Cl.
    *C07D 413/14*     (2006.01)
    *C07D 265/32*     (2006.01)
    *C07D 403/10*     (2006.01)

(52) U.S. Cl.
    CPC ......... *C07D 413/14* (2013.01); *C07D 265/32* (2013.01); *C07D 403/10* (2013.01)

(58) Field of Classification Search
    CPC ... C07D 413/14; C07D 265/32; C07D 403/10
    USPC .......................................... 544/123
    See application file for complete search history.

(56) References Cited

U.S. PATENT DOCUMENTS

2016/0102076 A1    4/2016   Suh et al.

FOREIGN PATENT DOCUMENTS

| | | |
|---|---|---|
| CN | 104788427 A | 7/2015 |
| KR | 10-2013-0006417 A | 1/2013 |
| WO | 2016/060443 A2 | 4/2016 |
| WO | 2016/173438 A1 | 11/2016 |
| WO | 2017/027768 A1 | 2/2017 |

*Primary Examiner* — Kristin A Vajda
(74) *Attorney, Agent, or Firm* — BakerHostetler

(57) ABSTRACT

The present invention provides a novel process for preparing an aminopyrimidine derivative or pharmaceutically acceptable salt thereof having a selective inhibitory activity against protein kinases, especially against the protein kinases for mutant epidermal growth factor receptors. And also, the present invention provides novel intermediates useful for said process and processes for preparing the same.

28 Claims, No Drawings

INTERMEDIATES USEFUL FOR THE SYNTHESIS OF AMINOPYRIMIDINE DERIVATIVES, PROCESS FOR PREPARING THE SAME, AND PROCESS FOR PREPARING AMINOPYRIMIDINE DERIVATIVES USING THE SAME

CROSS-REFERENCE TO RELATED APPLICATIONS

This application is the National Stage of International Patent Application No. PCT/KR2018/008381 filed Jul. 25, 2018, which claims the benefit of Korean application number 10-2017-0096220, filed Jul. 28, 2017, the entire contents of both of which are incorporated herein by reference.

TECHNICAL FIELD

The present invention relates to novel intermediates useful for the synthesis of aminopyrimidine derivatives and processes for preparing the same. And also, the present invention relates to a process for preparing an aminopyrimidine derivative or pharmaceutically acceptable salt thereof using said novel intermediates.

BACKGROUND ART

WO 2016/060443 has disclosed an aminopyrimidine derivative or pharmaceutically acceptable salt thereof having a selective inhibitory activity against protein kinases, especially against the protein kinases for mutant epidermal growth factor receptors. Said aminopyrimidine derivative or pharmaceutically acceptable salt thereof can provide an effective and safe therapy against non-small cell lung cancers. WO 2016/060443 has disclosed, as an aminopyrimidine derivative, for example N-(5-(4-(4-(((dimethylamino)methyl)-3-phenyl-1H-pyrazol-1-yl)pyrimidin-2-ylamino)-4-methoxy-2-morpholinophenyl)acrylamide of the following Formula 1 and a process for preparing the same.

<Formula 1>

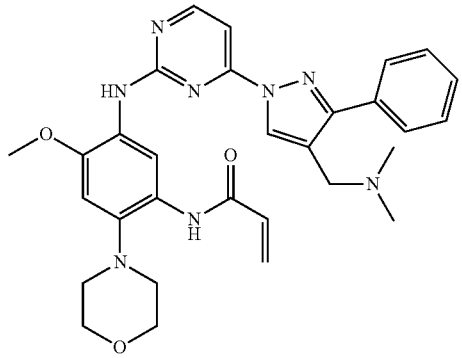

WO 2016/060443 has also disclosed a process for preparing the aminopyrimidine derivative of Formula (I), for example a process according to the following Reaction Scheme. In the following Reaction Scheme, $R_1$ may be methoxy, $R_2$ may be hydrogen, $R_3$ may be morpholinyl, $R_4$ may be hydrogen, $R_5$ may be phenyl, $R_6$ may be hydrogen, and $R_7$ may be dimethylamino.

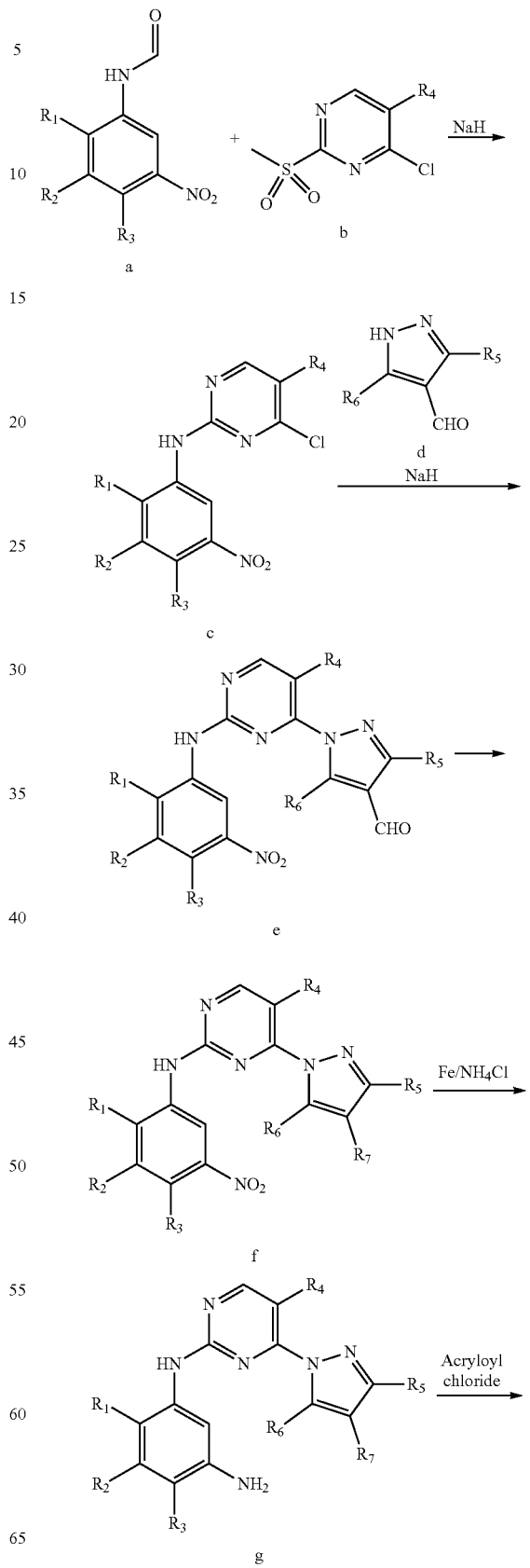

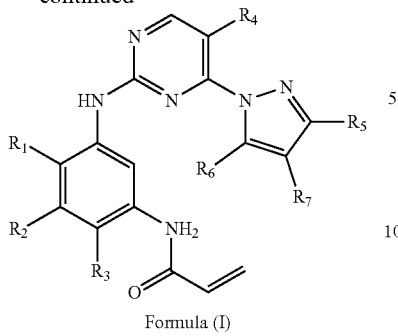

Formula (I)

Specifically, the process for preparing the compound of Formula (I) according to the above Reaction Scheme comprises reacting a compound of Formula (a) with a compound of Formula (b) by use of sodium hydride to obtain a compound of Formula (c); reacting the compound of Formula (c) with a compound of Formula (d) by use of sodium hydride to obtain a compound of Formula (e); performing reductive amination of the compound of Formula (e) to obtain a compound of Formula (f); reducing the compound of Formula (f) by use of iron and ammonium chloride to obtain a compound of Formula (g); and reacting the compound of Formula (g) with acryloyl chloride to obtain a compound of Formula (I).

Said process includes the reactions using sodium hydride, in order to prepare the compound of Formula (c) and the compound of Formula (e). However, since sodium hydride has a high possibility of fire and explosion, there is a problem that it is difficult to use in industrial mass production.

And also, said process includes the use of iron in the step for reducing the nitro group of the compound of Formula (f) to the amino group thereof. However, the use of iron may cause corrosion and contamination in a reactor, which makes it difficult to be applied to mass production. Further, during the reduction using iron and ammonium chloride to obtain the compound of the Formula (g), unknown tars and degradation products are produced; and the product (i.e., the compound of the Formula (g)) is obtained in black color. Therefore, in order to obtain the final product, the compound of formula (I), having a suitable purity, it is required to perform the purification process by column chromatography which is difficult to apply to mass production.

In addition, since acryloyl chloride used in the final step for preparing the compound of Formula (I) has low stability, it is difficult to handle at the production site. And also, since various degradation products are produced during the reaction of the compound of formula (g) with acryloyl chloride, it is difficult to prepare the compound of Formula (I) having a suitable purity.

DISCLOSURE OF INVENTION

Technical Problem

The present invention provides a novel process which is suitable for industrial mass production and which is able to produce N-(5-(4-(4-((dimethylamino)methyl)-3-phenyl-1H-pyrazol-1-yl)pyrimidin-2-ylamino)-4-methoxy-2-morpholinophenyl)acrylamide (the compound of Formula 1) or a pharmaceutically acceptable salt thereof with high purity and yield.

And also, the present invention provides novel intermediates useful for said process and processes for preparing the same.

Solution to Problem

According to an aspect of the present invention, there is provided a process for preparing N-(5-(4-(4-((dimethylamino)methyl)-3-phenyl-1H-pyrazol-1-yl)pyrimidin-2-ylamino)-4-methoxy-2-morpholinophenyl)acrylamide (the compound of formula 1) or a pharmaceutically acceptable salt thereof, the process comprising (a) reacting N-(5-(4-(4-formyl-3-phenyl-1H-pyrazol-1-yl)pyrimidin-2-ylamino)-4-methoxy-2-morpholinophenyl)acrylamide (the compound of formula 2) with dimethylamine or an acid addition salt thereof in the presences of a reducing agent and a base to form N-(5-(4-(4-((dimethylamino)methyl)-3-phenyl-1H-pyrazol-1-yl)pyrimidin-2-ylamino)-4-methoxy-2-morpholinophenyl)acrylamide (the compound of formula 1); and (b) isolating the N-(5-(4-(4-((dimethylamino)methyl)-3-phenyl-1H-pyrazol-1-yl)pyrimidin-2-ylamino)-4-methoxy-2-morpholinophenyl)acrylamide (the compound of formula 1) from the reaction mixture of Step (a).

In an embodiment, the N-(5-(4-(4-formyl-3-phenyl-1H-pyrazol-1-yl)pyrimidin-2-ylamino)-4-methoxy-2-morpholinophenyl)acrylamide (the compound of formula 2) may be obtained by reacting N-(5-formamido-4-methoxy-2-morpholinophenyl)acrylamide (the compound of formula 4) with 1-(2-(methylsulfonyl)pyrimidin-4-yl)-3-phenyl-1H-pyrazole-4-carbaldehyde (the compound of formula 10).

In another embodiment, the N-(5-formamido-4-methoxy-2-morpholinophenyl)acrylamide (the compound of formula 4) may be obtained by a process comprising (i) reacting N-(5-amino-2-methoxy-4-morpholinophenyl)formamide (the compound of formula 6) with a compound of Formula 14 to form a compound of Formula 5; and (ii) reacting the compound of Formula 5 with a base to obtain N-(5-formamido-4-methoxy-2-morpholinophenyl)acrylamide:

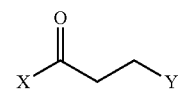
<Formula 14>

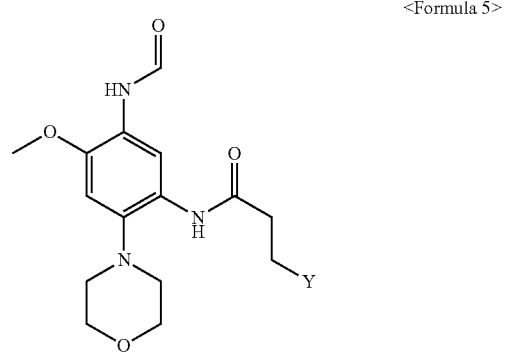
<Formula 5> wherein, X and Y are, independently of each other, halogen.

In still another embodiment, the N-(5-amino-2-methoxy-4-morpholinophenyl)formamide (the compound of formula 6) may be obtained by performing a reduction of N-(2-methoxy-4-morpholino-5-nitrophenyl)formamide (the compound of formula 7). The N-(2-methoxy-4-morpholino-5-nitrophenyl)formamide (the compound of formula 7) may be obtained by performing a formylation of 2-methoxy-4-morpholino-5-nitroaniline (the compound of formula 8).

In still another embodiment, the 1-(2-(methylsulfonyl)pyrimidin-4-yl)-3-phenyl-1H-pyrazole-4-carbaldehyde (the compound of formula 10) may be obtained by reacting 1-(2-(methylthio)pyrimidin-4-yl)-3-phenyl-1H-pyrazole-4-carbaldehyde with an oxidizing agent. The 1-(2-(methylthio)pyrimidin-4-yl)-3-phenyl-1H-pyrazole-4-carbaldehyde may be obtained by reacting 4-chloro-2-(methylthio)pyrimidine with 3-phenyl-1H-pyrazole-4-carbaldehyde.

According to another aspect of the present invention, there is provided N-(5-(4-(4-formyl-3-phenyl-1H-pyrazol-1-yl)pyrimidin-2-ylamino)-4-methoxy-2-morpholinophenyl)acrylamide (the compound of Formula 2).

According to still another aspect of the present invention, there is provided N-(5-formamido-4-methoxy-2-morpholinophenyl)acrylamide (the compound of Formula 4).

According to still another aspect of the present invention, there is provided a compound of Formula 5 or salt thereof:

<Formula 5> wherein, Y is halogen.

According to still another aspect of the present invention, there is provided N-(5-amino-2-methoxy-4-morpholinophenyl)formamide (the compound of Formula 6).

Advantageous Effects of Invention

The process of the present invention can effectively solve the problems involved in the prior art process, by preparing N-(5-(4-(4-((dimethylamino)methyl)-3-phenyl-1H-pyrazol-1-yl)pyrimidin-2-ylamino)-4-methoxy-2-morpholinophenyl)acrylamide (the compound of Formula 1) through novel intermediates, i.e., the compounds of Formulas 2, 4, 5 and 6. That is, the process of the present invention includes preparing the compound of Formula 5 from the compound of Formula 6; and then converting the compound of Formula 5 to the compound of Formula 4, thereby being able to avoid the use of acryloyl chloride. And also, in the process of the present invention, the removal and control of impurities can be easily performed. In addition, since the present invention may avoid the use of iron and ammonium chloride in the step for preparing the compound of Formula 6 (i.e., in the reduction step), said process is able to solve the problems of corrosion and contamination in a reactor which is caused by the use of iron; and therefore is suitable for industrial mass production.

BEST MODE FOR CARRYING OUT THE INVENTION

The present invention provides a process for preparing N-(5-((4(4-(4-(((dimethylamino)methyl)-3-phenyl-1H-pyrazol-1-yl)pyrimidin-2-yl)amino)-4-methoxy-2-morpholinophenyl)acrylamide or a pharmaceutically acceptable salt thereof, through novel intermediates. The overall reaction scheme of the process of the present invention is represented as the following Reaction Scheme 1.

<Reaction Scheme 1>

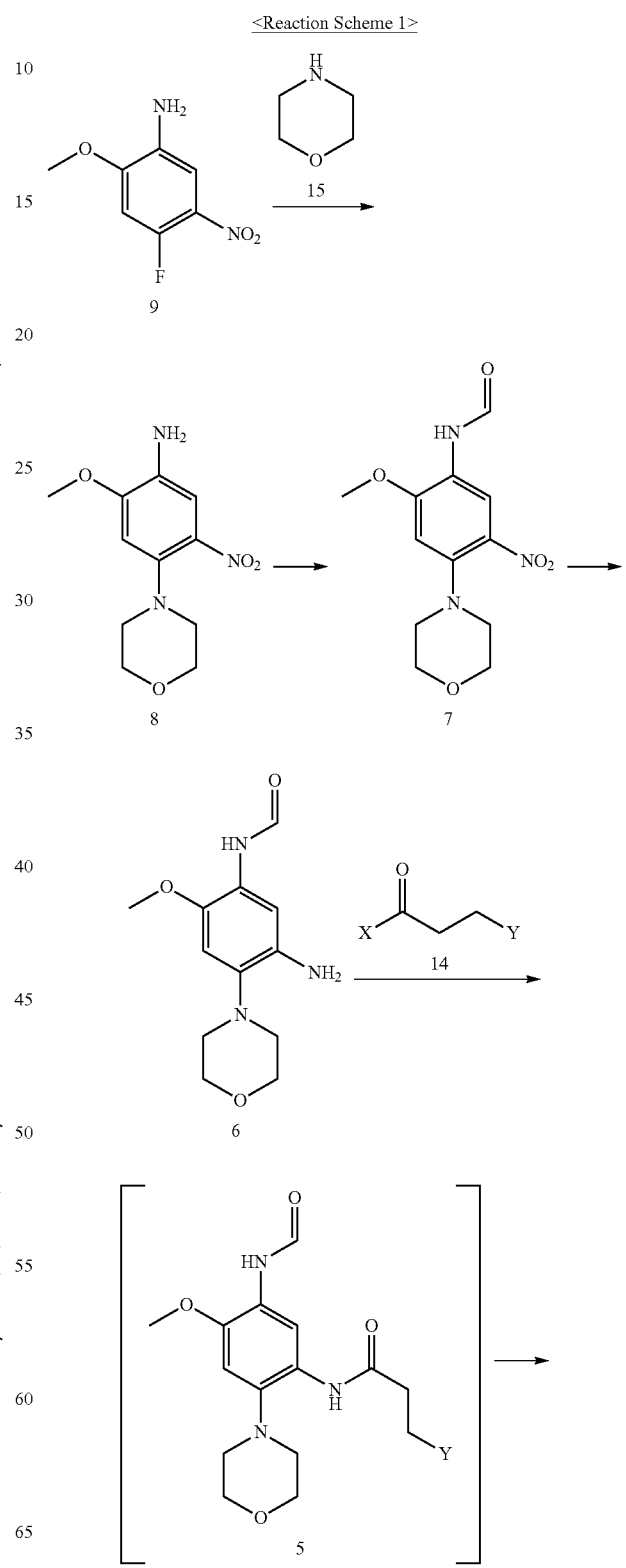

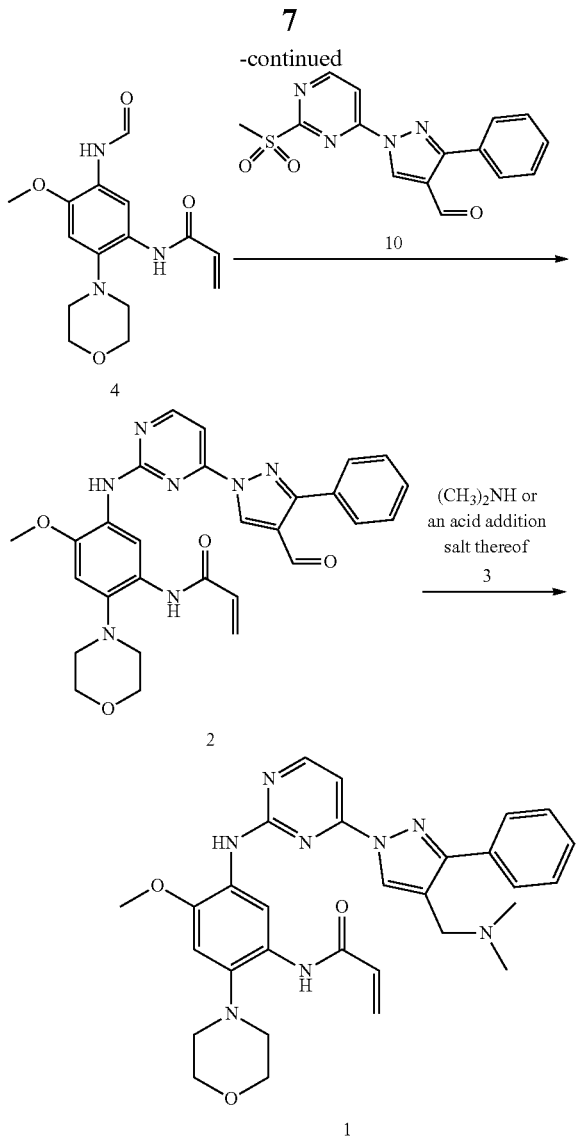

In the Reaction Scheme 1, X and Y are, independently of each other, halogen.

Hereinafter, the process of the present invention will be described in detail with reference to the respective steps of the Reaction Scheme 1.

The present invention provides a process for preparing N-(5-(4-(4-((dimethylamino)methyl)-3-phenyl-1H-pyrazol-1-yl)pyrimidin-2-ylamino)-4-methoxy-2-morpholinophenyl)acrylamide (the compound of formula 1) or a pharmaceutically acceptable salt thereof, the process comprising (a) reacting N-(5-(4-(4-formyl-3-phenyl-1H-pyrazol-1-yl)pyrimidin-2-ylamino)-4-methoxy-2-morpholinophenyl)acrylamide (the compound of formula 2) with dimethylamine or an acid addition salt thereof in the presences of a reducing agent and a base to form N-(5-(4-(4-((dimethylamino)methyl)-3-phenyl-1H-pyrazol-1-yl)pyrimidin-2-ylamino)-4-methoxy-2-morpholinophenyl)acrylamide (the compound of formula 1); and (b) isolating the N-(5-(4-(4-((dimethylamino)methyl)-3-phenyl-1H-pyrazol-1-yl)pyrimidin-2-ylamino)-4-methoxy-2-morpholinophenyl)acrylamide (the compound of formula 1) from the reaction mixture of Step (a).

In the process of the present invention, the reaction of Step (a) is a reductive amination. The reducing agent used in said reductive amination may be one or more selected from the group consisting of sodium triacetoxyborohydride, sodium cyanoborohydride, and sodium borohydride. Preferably, the reducing agent may be sodium triacetoxyborohydride. The reducing agent may be used in an amount ranging from 1.0 to 5.0 equivalents, preferably from 1.0 to 3.0 equivalents, per 1 equivalent of the compound of Formula 2, although the amount thereof may vary according to the reducing agents. The base used in said reaction may be one or more selected from the group consisting of sodium carbonate, sodium bicarbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic, 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine and diisopropylethylamine. Said reductive amination may be carried out in the presence of one or more solvent(s) selected from the group consisting of dimethylacetamide, dimethylformamide, dichloromethane, tetrahydrofuran, acetonitrile and ethyl acetate. And also, said reaction may be carried out at a temperature ranging from 0 to 50° C., preferably from 20 to 30° C. Therefore, the reaction may be carried out under a mild condition; and thus is suitable for industrial mass production.

The isolating of Step (b) may be carried out by crystallization from the reaction mixture of Step (a). For example, the isolating of Step (b) may be performed by crystallization through adding an antisolvent to the reaction mixture of Step (a). The antisolvent may be $C_1$~$C_5$ alcohol (for example, methanol, ethanol, isopropanol, butanol, and so on), water, or a mixture thereof, preferably water. Although the amount of the antisolvent to be used is not particularly limited, the antisolvent may be used for example in a weight ratio ranging from 2 to 20 times, preferably from 3 to 10 times, based on the compound of Formula 2. The isolating step may be also carried out at a temperature ranging from 0 to 40° C., preferably from 20 to 30° C. Therefore, the process of the present invention may be carried out under a mild condition; and thus is suitable for industrial mass production.

In the process of the present invention, the N-(5-(4-(4-formyl-3-phenyl-1H-pyrazol-1-yl)pyrimidin-2-ylamino)-4-methoxy-2-morpholinophenyl)acrylamide (the compound of formula 2) used in Step (a) may be obtained by reacting N-(5-formamido-4-methoxy-2-morpholinophenyl)acrylamide (the compound of formula 4) with 1-(2-(methylsulfonyl)pyrimidin-4-yl)-3-phenyl-1H-pyrazole-4-carbaldehyde (the compound of formula 10). The reaction of the compound of Formula 4 with the compound of Formula 10 may be carried out in the presence of one or more base(s) selected from the group consisting of sodium hydride, sodium $C_1$~$C_6$ alkoxide, potassium $C_1$~$C_6$ alkoxide, sodium carbonate, potassium carbonate, lithium carbonate, cesium carbonate, sodium bicarbonate, potassium bicarbonate, potassium phosphate, 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, dimethylaminopyridine, and triethylamine, preferably sodium $C_1$~$C_6$ alkoxide or potassium $C_1$~$C_6$ alkoxide, more preferably sodium $C_1$~$C_6$ alkoxide. The base may be used in an amount ranging from 1 to 5 moles, preferably from 1.0 to 2.0 moles, per 1 mole of the compound of Formula 4. And also, the reaction of the compound of formula 4 with the compound of formula 10 may be carried out in the presence of an inert solvent, e.g., in the presence of one or more solvent(s) selected from the group consisting of dimethylformamide, dimethylacetamide, dichloromethane, dimethyl sulfoxide, tetrahydrofuran, hexamethylphosphoramide, $C_1\text{~}C_5$ alcohol, diethyl ether, ethyl acetate, acetonitrile and acetone. Preferably, the reaction may be carried out in dimethylformamide or tetrahydrofuran. And also, the reaction may be carried out at a temperature ranging from 0 to 50° C., preferably from 0 to 30° C.

In the process of the present invention, the N-(5-formamido-4-methoxy-2-morpholinophenyl)acrylamide (the compound of formula 4) may be obtained by a process comprising (i) reacting N-(5-amino-2-methoxy-4-morpholinophenyl)formamide (the compound of formula 6) with a compound of Formula 14 to form a compound of Formula 5; and (ii) reacting the compound of Formula 5 with a base to obtain N-(5-formamido-4-methoxy-2-morpholinophenyl)acrylamide:

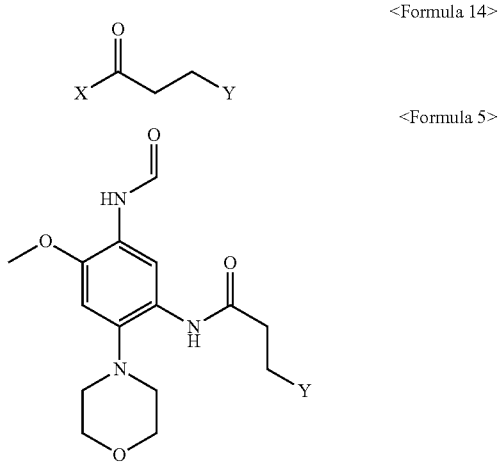

<Formula 14>

<Formula 5> wherein, X and Y are, independently of each other, halogen.

In an embodiment of the process of the present invention, Step (i) and Step (ii) may be carried out in a one-pot reaction, without isolating the compound of Formula 5. Therefore, the process of the present invention is suitable for industrial mass production.

The reacting of Step (i), i.e., the reaction of the compound of Formula 6 with the compound of Formula 14, may be carried out in the presence of one or more base(s) selected from the group consisting of potassium tert-butoxide, sodium hydroxide, potassium hydroxide, sodium hydride, sodium carbonate, sodium bicarbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine and diisopropylethylamine. The base may be used in an amount ranging from 1 to 5 equivalents, preferably from 1 to 3 equivalents, per 1 equivalent of the compound of Formula 6. The reaction may be carried out in the presence of one or more solvent(s) selected from the group consisting of acetone, acetonitrile, methyl ethyl ketone, dimethylformamide, dimethylacetamide, dichloromethane, dimethyl sulfoxide, dimethylsulfonamide, tetrahydrofuran, hexamethylphosphoramide, $C_1\text{~}C_5$ alcohol, dimethyl ether, diethyl ether, diisopropyl ether, ethyl acetate, dimethoxyethane and toluene. Preferably, the solvent may be acetone, acetonitrile, methyl ethyl ketone, or $C_1\text{~}C_5$ alcohol (such as methanol, ethanol, propanol, isopropyl alcohol, butanol, and so on). More preferably, the solvent may be acetonitrile. The reaction may be carried out at a temperature ranging from 0 to 100° C., preferably from 10 to 30° C.

In the reacting of Step (ii), i.e., the reaction of the compound of Formula 5 with a base, the base may be one or more selected from the group consisting of potassium tert-butoxide, sodium hydroxide, potassium hydroxide, lithium hydroxide, sodium hydride, sodium carbonate, sodium bicarbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine and diisopropylethylamine. The base may be preferably sodium hydroxide, triethylamine or diisopropylamine, more preferably triethylamine. The base may be used in an amount ranging from 1 to 20 equivalents, preferably from 5 to 10 equivalents, per 1 equivalent of the compound of Formula 6. And also, the reaction may be carried out in the presence of a solvent selected from the group consisting of acetonitrile, methyl ethyl ketone, acetone, methyl isobutyl ketone, dichloromethane, dichloroethane, dimethylformamide, dimethylacetamide, dimethyl sulfoxide, tetrahydrofuran, $C_1\text{~}C_5$ alcohol, toluene, ethyl acetate, isopropyl acetate, diethyl ether, water and a mixture thereof. Preferably, the solvent may be selected from the group consisting of $C_1\text{~}C_5$ alcohol, acetonitrile, tetrahydrofuran, methyl ethyl ketone, acetone, dichloromethane, water and a mixture thereof. More preferably, the solvent may be $C_1\text{~}C_5$ alcohol. The reacting of the compound of Formula 5 with the base may be carried out at a temperature ranging from 40 to 150° C., preferably at a temperature ranging from 60 to 100° C., more preferably at the reflux temperature of the used solvent.

In the process of the present invention, the N-(5-amino-2-methoxy-4-morpholinophenyl)formamide (the compound of formula 6) may be obtained by performing a reduction of N-(2-methoxy-4-morpholino-5-nitrophenyl)formamide (the compound of formula 7). The reduction may be carried out with a reducing agent selected from the group consisting of formic acid and ammonium formate. The reducing agent may be in amount ranging from 1 to 15 equivalents per 1 equivalent of the compound of Formula 7. And also, the reduction may be carried out in the presence of a catalyst selected from the group consisting of palladium, palladium/carbon, zinc, copper, magnesium, and platinum, preferably in the presence of palladium/carbon. The reaction may be carried out in the presence of an inert solvent, for example in the presence of one or more solvent(s) selected from the group consisting of dimethylformamide, dimethylacetamide, dichloromethane, dimethyl sulfoxide, tetrahydrofuran, hexamethylphosphoramide, $C_1\text{~}C_5$ alcohol, diethyl ether, ethyl acetate, acetonitrile and acetone. Preferably, the solvent may be tetrahydrofuran and/or ethanol. And also, the reaction may be carried out at a temperature ranging from 0 to 50° C., preferably 20 to 30° C.

In the process of the present invention, the N-(2-methoxy-4-morpholino-5-nitrophenyl)formamide (the compound of formula 7) may be obtained by performing a formylation of 2-methoxy-4-morpholino-5-nitroaniline (the compound of formula 8). The formylation may be carried out with a mixture of acetic acid (e.g., anhydrous acetic acid) and formic acid. Each amount of acetic acid and formic acid to be used may range from 2 to 5 moles, preferably from 2.5 to 3.5 moles, per 1 mole of the compound of Formula 8. And also, the formylation may be carried out in the presence of an inert solvent, for example in the presence of one or more solvent(s) selected from the group consisting of dimethylformamide, dimethylacetamide, dichloromethane, dimethyl sulfoxide, tetrahydrofuran, hexamethylphosphoramide, $C_1$~$C_5$ alcohol, diethyl ether, ethyl acetate, acetonitrile and acetone. Preferably, the solvent may be dimethylformamide, dimethylacetamide, tetrahydrofuran, or a mixture thereof. And also, the reaction may be carried out at a temperature ranging from 0 to 70° C., preferably from 20 to 50° C.

In the process of the present invention, the 2-methoxy-4-morpholino-5-nitroaniline (the compound of Formula 8) may be obtained by reacting 4-fluoro-2-methoxy-5-nitroaniline (the compound of Formula 9) with morpholine (the compound of Formula 15). The reaction may be carried out in the presence of one or more base(s) selected from the group consisting of sodium $C_1$~$C_6$ alkoxide, potassium $C_1$~$C_6$ alkoxide, sodium carbonate, potassium carbonate, lithium carbonate, cesium carbonate, sodium bicarbonate, potassium bicarbonate, potassium phosphate, 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, dimethylaminopyridine, triethylamine and diisopropylethylamine. Preferably, the base may be triethylamine or diisopropylethylamine. The reaction may be carried out in the presence of an inert solvent, for example in the presence of one or more solvent(s) selected from the group consisting of dimethylformamide, dimethylacetamide, dichloromethane, dimethyl sulfoxide, tetrahydrofuran, hexamethylphosphoramide, $C_1$~$C_5$ alcohol, diethyl ether, ethyl acetate, acetonitrile and acetone. Preferably, the solvent may be acetonitrile or tetrahydrofuran. And also, the reaction may be carried out at a temperature ranging from 0 to 100° C., preferably from 70 to 80° C.

In an embodiment, the compound of Formula 10 used as an intermediate in Reaction Scheme 1 may be prepared according to the following Reaction Scheme 2.

<Reaction Scheme 2>

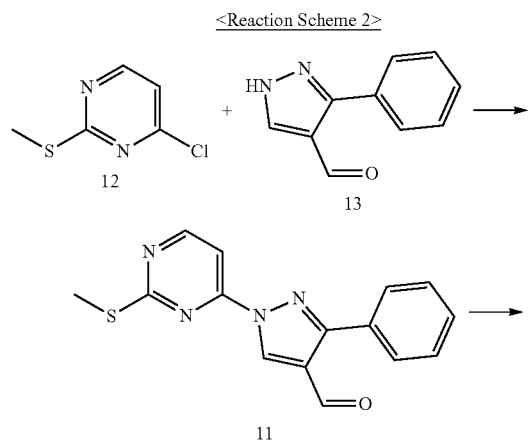

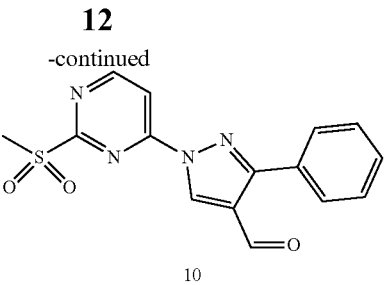

The 1-(2-(methylsulfonyl)pyrimidin-4-yl)-3-phenyl-1H-pyrazole-4-carbaldehyde (the compound of formula 10) may be obtained by reacting 1-(2-(methylthio)pyrimidin-4-yl)-3-phenyl-1H-pyrazole-4-carbaldehyde (the compound of Formula 11) with an oxidizing agent. The oxidizing agent may be one or more selected from the group consisting of potassium permanganate, chromic acid, oxygen, hydrogen peroxide and 3-chloroperbenzoic acid. Preferably, the oxidizing agent may be hydrogen peroxide. The amount of the oxidizing agent to be used may range from 1.8 to 10.0 moles, preferably from 2.0 to 5.0 moles, per 1 mole of the compound of Formula 17. And also, the reaction rate can be increased by performing the oxidation in the presence of a catalyst such as ammonium molybdate tetrahydrate. The reaction may be carried out in the presence of one or more solvent(s) selected from the group consisting of $C_1$~$C_5$ alcohol, carbon tetrachloride, chloroform, dichloromethane, acetone, methyl ethyl ketone, methyl isobutyl ketone, cyclohexanone, pentane, hexane, heptane, octane, nonane, decane, undecane, dodecane, cyclohexane, petroleum ether, kerosene, toluene, xylene, mesitylene and benzene.

The 1-(2-(methylthio)pyrimidin-4-yl)-3-phenyl-1H-pyrazole-4-carbaldehyde (the compound of Formula 11) may be obtained by reacting 4-chloro-2-(methylthio)pyrimidine (the compound of Formula 12) with 3-phenyl-1H-pyrazole-4-carbaldehyde (the compound of Formula 13). The reacting the compound of Formula 12 with the compound of Formula 13 may be carried out in the presence of one or more base(s) selected from the group consisting of potassium tertbutoxide, sodium hydroxide, potassium hydroxide, sodium hydride, sodium carbonate, potassium carbonate, potassium phosphate (including potassium phosphate monobasic, potassium phosphate dibasic, and potassium phosphate tribasic), sodium phosphate (including sodium phosphate monobasic, sodium phosphate dibasic, and sodium phosphate tribasic), 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, triethylamine, diisopropylamine and diisopropylethylamine. Preferably, the base may be selected from the group consisting of sodium carbonate, potassium carbonate, and potassium phosphate. The reaction may be carried out in the presence of one or more solvent(s) selected from the group consisting of dichloromethane, dichloroethane, dimethylformamide, dimethylacetamide, dimethyl sulfoxide, tetrahydrofuran, $C_1$~$C_5$ alcohol, ethyl acetate, acetone, methyl ethyl ketone, acetonitrile and toluene. Preferably, the solvent may be selected from the group consisting of dichloromethane, dimethylformamide and dimethylacetamide. More preferably, the solvent may be dimethylformamide. And also, the reaction may be carried out at a temperature ranging from 0 to 100° C., preferably from 40 to 60° C.

The present invention includes, within its scope, novel intermediates useful for said novel processes.

That is, the present invention provides N-(5-(4-(4-formyl-3-phenyl-1H-pyrazol-1-yl)pyrimidin-2-ylamino)-4-methoxy-2-morpholinophenyl)acrylamide (the compound of Formula 2).

And also, the present invention provides N-(5-formamido-4-methoxy-2-morpholinophenyl)acrylamide (the compound of Formula 4).

And also, the present invention provides a compound of Formula 5 or salt thereof:

<Formula 5>

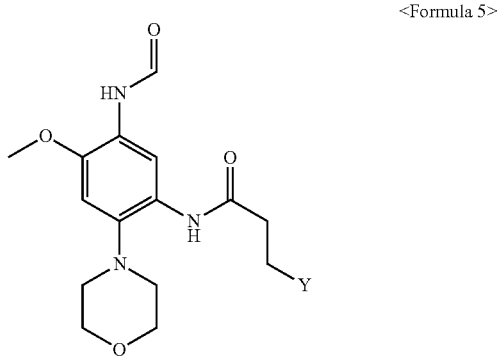

wherein, Y is halogen.

And also, the present invention provides N-(5-amino-2-methoxy-4-morpholinophenyl)formamide (the compound of Formula 6).

The following examples are provided for illustration purposes only, and are not intended to limit the scope of the invention.

Example 1. Preparation of 2-methoxy-4-morpholino-5-nitroaniline (Compound 8)

A mixture of 4-fluoro-2-methoxy-5-nitroaniline (60.0 g, 0.322 mol), acetonitrile (600.0 mL), diisopropylethylamine (93.3 g, 0.623 mol), and morpholine (84.2 g, 0.967 mol) was refluxed under stirring for 4 hours. To the reaction mixture, was purified water (1.8 L) added. The resulting solid was filtered and then dried in vacuo to obtain 78.0 g of the titled compound. (Yield: 96.0%)

$^1$H-NMR (400 MHz, DMSO) δ 7.21 (s, 1H), 6.76 (s, 1H), 5.03 (s, 2H), 3.89 (s, 3H), 3.69 (t, 4H), 2.92 (t, 4H)

Example 2. Preparation of N-(2-methoxy-4-morpholino-5-nitrophenyl)formamide (Compound 7)

A mixture of anhydrous acetic acid (254.0 g, 2.487 mol) and formic acid (137.4 g, 2.984 mol) was stirred at 50° C. for 30 minutes. 2-Methoxy-4-morpholino-5-nitroaniline (210.0 g, 0.829 mol) and tetrahydrofuran (219 mL) were added to the reaction mixture, which was then stirred at 20-25° C. for 1 hour. To the reaction mixture, was methyl tertbutyl ether (2.1 L) added. The resulting solid was filtered and then dried in vacuo to obtain 211.0 g of the titled compound. (Yield: 91.0%)

$^1$H-NMR (400 MHz, DMSO) δ 9.88 (s, 1H), 8.85 (s, 1H), 8.29 (d, 1H), 6.83 (s, 1H), 3.99 (s, 1H), 3.72-3.74 (t, 4H), 3.03-3.05 (t, 4H)

Example 3. N-(5-amino-2-methoxy-4-morpholinophenyl)formamide (Compound 6)

A mixture of N-(2-methoxy-4-morpholino-5-nitrophenyl)formamide (100.0 g, 0.356 mol), ethanol (700.0 mL), tetrahydrofuran (700.0 mL), 10% palladium/carbon (5.0 g), and ammonium formate (200.0 g) was stirred at room temperature for 1 hour. The reaction mixture was stirred at 40° C. for 2 hours and then filtered using diatomaceous earth. The resulting filtrate was concentrated under reduced pressure. Dichloromethane (1.4 L) and purified water (1.0 L) were added to the resulting residue, which was then stirred. The separated organic layer was concentrated under reduced pressure to obtain 61.0 g of the titled compound. (Yield: 68.3%)

$^1$H-NMR (400 MHz, DMSO) δ 9.33 (s, 1H), 8.20 (s, 1H), 7.58 (s, 1H), 6.66 (s, 1H), 4.49 (s, 2H), 3.73 (m, 7H), 2.77 (t, 4H)

Example 4. Preparation of 1-(2-(methylthio)pyrimidin-4-yl)-3-phenyl-1H-pyrazole-4-carbaldehyde (Compound 11)

A mixture of 4-chloro-2-(methylthio)pyrimidine (102.6 g, 0.639 mol), 3-phenyl-1H-pyrazole-4-carbaldehyde (100.0 g, 0.581 mol), potassium carbonate (160.5 g, 1.162 mol), and dimethylformamide (700 mL) was stirred at 40-50° C. for 2 hours. Purified water (1.6 L) was slowly added to the reaction mixture, which was then stirred at room temperature for 2 hours. The resulting solid was filtered and then dried in vacuo to obtain 154.0 g of the titled compound. (Yield: 89.5%)

$^1$H-NMR (400 MHz, CDCl$_3$) δ 10.10 (s, 1H), 9.20 (s, 1H), 8.65 (d, 1H), 7.84-7.86 (m, 2H), 7.67-7.71 (m, 3H), 2.65 (s, 3H)

Example 5. Preparation of 1-(2-(methylsulfonyl)pyrimidin-4-yl)-3-phenyl-1H-pyrazole-4-carbaldehyde (Compound 10)

A 35% hydrogen peroxide solution (3.4 g, 30.3 mmol) and ammonium molybdate tetrahydrate (0.4 g, 0.3 mmol) were added to a solution of 1-(2-(methylthio)pyrimidin-4-yl)-3-phenyl-1H-pyrazole-4-carbaldehyde (3.0 g, 10.1 mmol) in ethanol (21.0 mL). The reaction mixture was stirred for 2 hours and then extracted with dichloromethane (30.0 mL) and purified water (30.0 mL). The separated organic layer was washed with a 10% sodium sulfite solution (21.0 mL) and purified water and then concentrated under reduced pressure. The resulting residue was crystallized by adding isopropyl alcohol thereto. The resulting solid was filtered and then dried in vacuo to obtain 2.8 g of the titled compound. (Yield: 84.3%)

$^1$H-NMR (400 MHz, CDCl$_3$) δ 10.12 (s, 1H), 9.30 (s, 1H), 9.00 (d, 1H), 8.27 (d, 2H), 7.87-7.93 (m, 2H), 7.48-7.54 (m, 3H), 3.44 (s, 3H)

Example 6. Preparation of N-(5-formamido-4-methoxy-2-morpholinophenyl)acrylamide (Compound 4)

A mixture of N-(5-amino-2-methoxy-4-morpholinophenyl)formamide (20.0 g, 0.080 mol), acetonitrile (200.0 mL), sodium bicarbonate (20.0 g, 0.239 mol), and 3-chloropropionyl chloride (13.1 g, 0.103 mol) was stirred at 20-30° C. for 30 minutes. Dichloromethane (300.0 mL) and purified water (200.0 mL) were added to the reaction mixture, which was then stirred. The separated organic layer was concentrated under reduced pressure to prepare 3-chloro-N-(5-formamido-4-methoxy-2-morpholinophenyl)propanamide (Compound 5) and then n-propanol (140.0 mL) and triethylamine (80.5 g, 0.796 mol) were added thereto, followed by refluxing under stirring for 3 hours. The reaction mixture was cooled to room temperature. The resulting solid was filtered and then dried in vacuo to obtain 24.2 g of the titled compound. (Yield: 99.6%)

$^1$H-NMR (400 MHz, DMSO) δ 10.49 (br, 1H), 9.55 (s, 1H), 9.09 (s, 1H), 8.58 (s, 1H), 8.24 (s, 1H), 6.83 (s, 1H), 6.62 (dd, 1H), 6.21 (d, 1H), 5.71 (d, 1H), 3.85 (s, 3H), 3.76 (t, 4H), 2.82 (t, 4H)

Example 7. Preparation of N-(5-(4-(4-formyl-3-phenyl-1H-pyrazol-1-yl)pyrimidin-2-ylamino)-4-methoxy-2-morpholinophenyl)acrylamide (Compound 2)

A mixture of N-(5-formamido-4-methoxy-2-morpholinophenyl)acrylamide (15.0 g, 0.049 mol), tetrahydrofuran (125.0 mL), 1-(2-(methylsulfonyl)pyrimidin-4-yl)-3-phenyl-1H-pyrazole-4-carbaldehyde (17.7 g, 0.054 mol), and sodium tert-butoxide (4.5 g, 0.054 mol) was stirred at 20-30° C. for 1 hour. A 2N NaOH solution (45.0 mL) was added to the reaction mixture, which was then stirred at room temperature for 15 hours. Purified water (75.0 mL) was slowly added to the reaction mixture, which was then stirred at 20-30° C. for 2 hours. The resulting solid was filtered and then dried in vacuo to obtain 14.4 g of the titled compound. (Yield: 55.8%)

$^1$H-NMR (400 MHz, DMSO) δ 10.15 (s, 1H), 9.95 (br, 1H), 9.17 (s, 1H), 8.98 (br, 1H), 8.62 (d, 1H), 8.37 (s, 1H), 8.02 (m, 2), 7.51 (m, 3H), 7.38 (d, 1H), 6.94 (s, 1H), 6.73 (dd, 1H), 6.30 (d, 1H), 5.80 (d, 1H), 3.90 (s, 3H), 3.82 (t, 4H), 2.86 (t, 4H)

Example 8. Preparation of N-(5-(4-(4-((dimethylamino)methyl)-3-phenyl-1H-pyrazol-1-yl)pyrimidin-2-ylamino)-4-methoxy-2-morpholinophenyl)acrylamide (Compound 1)

A mixture of N-(5-(4-(4-foryl-3-phenyl-1H-pyrazol-1-yl)pyrimidin-2-ylamino)-4-methoxy-2-morpholinophenyl)acrylamide (3.0 g, 0.006 mol), dimethylacetamide (30.0 mL), dimethylamine hydrochloride (0.9 g, 0.011 mol), and diisopropylethylamine (3.7 g, 0.029 mol) was stirred at 20-30° C. for 1 hour. Sodium triacetoxyborohydride (3.6 g, 0.017 mol) was added to the reaction mixture, which was then stirred at 20-30° C. for 1 hour. Purified water (30.0 mL) was added to the reaction mixture, which was then stirred for 1 hour. The resulting solid was filtered under reduced pressure and then dried in vacuo to obtain 2.9 g of the titled compound. (Yield: 92.0%)

$^1$H-NMR (400 MHz, DMSO) δ 9.15 (s, 2H), 9.08 (s, 1H), 8.54 (d, 1H), 8.18 (s, 1H), 8.05 (d, 2H), 7.48 (m, 2H), 7.36 (m, 1H), 7.34 (d, 1H), 6.96 (s, 1H), 6.74 (q, 1H), 6.44 (d, 1H), 5.85 (d, 1H), 3.91 (s, 3H), 3.82 (s, 4H), 3.46 (1s, 1H), 2.86 (s, 4H), 2.21 (s, 6H)

The invention claimed is:

1. A process for preparing N-(5-(4-(4-((dimethylamino)methyl)-3-phenyl-1H-pyrazol-1-yl)pyrimidin-2-ylamino)-4-methoxy-2-morpholinophenyl)acrylamide or a pharmaceutically acceptable salt thereof, the process comprising
   (a) reacting N-(5-(4-(4-formyl-3-phenyl-1H-pyrazol-1-yl)pyrimidin-2-ylamino)-4-methoxy-2-morpholinophenyl)acrylamide with dimethylamine or an acid addition salt thereof in the presences of a reducing agent and a base to form N-(5-(4-(4-((dimethylamino)methyl)-3-phenyl-1H-pyrazol-1-yl)pyrimidin-2-ylamino)-4-methoxy-2-morpholinophenyl)acrylamide; and
   (b) isolating the N-(5-(4-(4-((dimethylamino)methyl)-3-phenyl-1H-pyrazol-1-yl)pyrimidin-2-ylamino)-4-methoxy-2-morpholinophenyl)acrylamide from the reaction mixture of Step (a).

2. The process according to claim 1, wherein the reducing agent is one or more selected from the group consisting of sodium triacetoxyborohydride, sodium cyanoborohydride, and sodium borohydride.

3. The process according to claim 1, wherein the reducing agent is used in a ratio ranging from 1 to 5 equivalent(s) per 1 equivalent of N-(5-(4-(4-formyl-3-phenyl-1H-pyrazol-1-yl)pyrimidin-2-ylamino)-4-methoxy-2-morpholinophenyl)acrylamide.

4. The process according to claim 1, wherein the base is one or more selected from the group consisting of sodium carbonate, sodium bicarbonate, potassium carbonate, potassium phosphate, sodium phosphate, 1,8-diazabicyclo[5.4.0]undec-7-ene, 1,4-diazabicyclo[2.2.2]octane, 1,5-diazabicyclo[4.3.0]non-5-ene, pyridine, triethylamine, diisopropylamine and diisopropylethylamine.

5. The process according to claim 1, wherein the reacting of Step (a) is carried out in the one or more solvent(s) selected from the group consisting of dimethylacetamide, dimethylformamide, dichloromethane, tetrahydrofuran, acetonitrile and ethyl acetate.

6. The process according to claim 1, wherein the isolating of Step (b) is carried out by crystallization through adding an antisolvent to the reaction mixture of Step (a).

7. The process according to claim 6, wherein the antisolvent is $C_1$~$C_5$ alcohol, water, or a mixture thereof.

8. The process according to claim 1, wherein the N-(5-(4-(4-formyl-3-phenyl-1H-pyrazol-1-yl)pyrimidin-2-ylamino)-4-methoxy-2-morpholinophenyl)acrylamide is obtained by reacting N-(5-formamido-4-methoxy-2-morpholinophenyl)acrylamide with 1-(2-(methylsulfonyl)pyrimidin-4-yl)-3-phenyl-1H-pyrazole-4-carbaldehyde.

9. The process according to claim 8, wherein the reacting is carried out in the presence of one or more base(s) selected from the group consisting of sodium hydride, sodium $C_1$~$C_6$ alkoxide, potassium $C_1$~$C_6$ alkoxide, sodium carbonate, potassium carbonate, lithium carbonate, cesium carbonate, sodium bicarbonate, potassium bicarbonate, potassium phosphate, 1,8-diazabicyclo[5.4.0]undec-7-ene, 1,4-diazabicyclo[2.2.2]octane, 1,5-diazabicyclo[4.3.0]non-5-ene, pyridine, dimethylaminopyridine, and triethylamine.

10. The process according to claim 8, wherein the N-(5-formamido-4-methoxy-2-morpholinophenyl)acrylamide is obtained by a process comprising
   (i) reacting N-(5-amino-2-methoxy-4-morpholinophenyl)formamide with a compound of Formula 14 to form a compound of Formula 5; and
   (ii) reacting the compound of Formula 5 with a base to obtain N-(5-formamido-4-methoxy-2-morpholinophenyl)acrylamide:

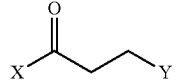

<Formula 14>

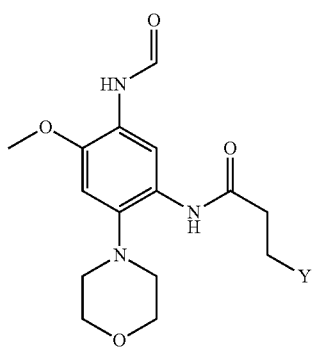

wherein, X and Y are, independently of each other, halogen.

11. The process according to claim 10, wherein Step (i) and Step (ii) are carried out in a one-pot reaction without isolating the compound of Formula 5.

12. The process according to claim 10, wherein the reacting of Step (i) is carried out in the presence of one or more base(s) selected from the group consisting of potassium tert-butoxide, sodium hydroxide, potassium hydroxide, sodium hydride, sodium carbonate, sodium bicarbonate, potassium carbonate, potassium phosphate, sodium phosphate, 1,8-diazabicyclo[5.4.0]undec-7-ene, 1,4-diazabicyclo[2.2.2]octane, 1,5-diazabicyclo[4.3.0]non-5-ene, pyridine, triethylamine, diisopropylamine and diisopropylethylamine.

13. The process according to claim 10, wherein the base used in Step (ii) is one or more selected from the group consisting of potassium tert-butoxide, sodium hydroxide, potassium hydroxide, lithium hydroxide, sodium hydride, sodium carbonate, sodium bicarbonate, potassium carbonate, potassium phosphate, sodium phosphate, 1,8-diazabicyclo[5.4.0]undec-7-ene, 1,4-diazabicyclo[2.2.2]octane, 1,5-diazabicyclo[4.3.0]non-5-ene, pyridine, triethylamine, diisopropylamine and diisopropylethylamine.

14. The process according to claim 10, wherein the N-(5-amino-2-methoxy-4-morpholinophenyl)formamide is obtained by performing a reduction of N-(2-methoxy-4-morpholino-5-nitrophenyl)formamide.

15. The process according to claim 14, wherein the reduction is carried out with a reducing agent selected from the group consisting of formic acid and ammonium formate.

16. The process according to claim 14, wherein the reduction is carried out in the presence of a catalyst selected from the group consisting of palladium, palladium/carbon, zinc, copper, magnesium, and platinum.

17. The process according to claim 14, wherein the N-(2-methoxy-4-morpholino-5-nitrophenyl)formamide is obtained by performing a formylation of 2-methoxy-4-morpholino-5-nitroaniline.

18. The process according to claim 17, wherein the formylation is carried out with a mixture of acetic acid and formic acid.

19. The process according to claim 8, wherein the 1-(2-(methylsulfonyl)pyrimidin-4-yl)-3-phenyl-1H-pyrazole-4-carbaldehyde is obtained by reacting 1-(2-(methylthio)pyrimidin-4-yl)-3-phenyl-1H-pyrazole-4-carbaldehyde with an oxidizing agent.

20. The process according to claim 19, wherein the oxidizing agent is one or more selected from the group consisting of potassium permanganate, chromic acid, oxygen, hydrogen peroxide and 3-chloroperbenzoic acid.

21. The process according to claim 19, wherein the reacting is carried out in the presence of one or more solvent(s) selected from the group consisting of $C_1$~$C_5$ alcohol, carbon tetrachloride, chloroform, dichloromethane, acetone, methyl ethyl ketone, methyl isobutyl ketone, cyclohexanone, pentane, hexane, heptane, octane, nonane, decane, undecane, dodecane, cyclohexane, petroleum ether, kerosene, toluene, xylene, mesitylene and benzene.

22. The process according to claim 19, wherein the 1-(2-(methylthio)pyrimidin-4-yl)-3-phenyl-1H-pyrazole-4-carbaldehyde is obtained by reacting 4-chloro-2-(methylthio)pyrimidine with 3-phenyl-1H-pyrazole-4-carbaldehyde.

23. The process according to claim 22, wherein the reacting is carried out in the presence of one or more base(s) selected from the group consisting of potassium tert-butoxide, sodium hydroxide, potassium hydroxide, sodium hydride, sodium carbonate, potassium carbonate, potassium phosphate, sodium phosphate, 1,8-diazabicyclo[5.4.0]undec-7-ene, 1,4-diazabicyclo[2.2.2]octane, 1,5-diazabicyclo[4.3.0]non-5-ene, pyridine, triethylamine, diisopropylamine and diisopropylethylamine.

24. The process according to claim 22, wherein the reacting is carried out in the presence of one or more solvent(s) selected from the group consisting of dichloromethane, dichloroethane, dimethylformamide, dimethylacetamide, dimethyl sulfoxide, tetrahydrofuran, $C_1$~$C_5$ alcohol, ethyl acetate, acetone, methyl ethyl ketone, acetonitrile and toluene.

25. A compound, wherein said compound is N-(5-(4-(4-formyl-3-phenyl-1H-pyrazol-1-yl)pyrimidin-2-ylamino)-4-methoxy-2-morpholinophenyl)acrylamide.

26. A compound, wherein said compound is N-(5-formamido-4-methoxy-2-morpholinophenyl)acrylamide.

27. A compound of Formula 5 or salt thereof:

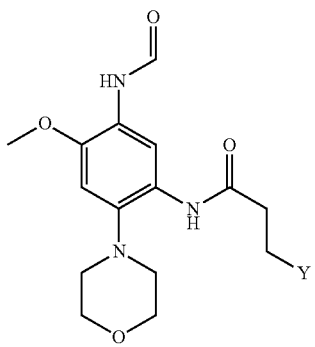

wherein, Y is halogen.

28. A compound, wherein said compound is N-(5-amino-2-methoxy-4-morpholinophenyl)formamide.

* * * * *